(12) United States Patent
Breuer et al.

(10) Patent No.: US 8,455,223 B2
(45) Date of Patent: Jun. 4, 2013

(54) DEHYDROGENASES, THE DERIVATIVES THEREOF, AND METHOD FOR THE PRODUCTION OF OPTICALLY ACTIVE ALKANOLS

(75) Inventors: Michael Breuer, Darmstadt (DE); Thomas Friedrich, Darmstadt (DE); Maria Kesseler, Mannheim (DE)

(73) Assignee: BASF SE, Ludwigshafen (DE)

( * ) Notice: Subject to any disclaimer, the term of this patent is extended or adjusted under 35 U.S.C. 154(b) by 288 days.

(21) Appl. No.: 11/992,169

(22) PCT Filed: Sep. 14, 2006

(86) PCT No.: PCT/EP2006/066336
§ 371 (c)(1),
(2), (4) Date: Mar. 18, 2008

(87) PCT Pub. No.: WO2007/033928
PCT Pub. Date: Mar. 29, 2007

(65) Prior Publication Data
US 2008/0220484 A1 Sep. 11, 2008

(30) Foreign Application Priority Data
Sep. 19, 2005 (DE) .......................... 10 2005 044 736

(51) Int. Cl.
| | | |
|---|---|---|
| C12P 7/00 | (2006.01) | |
| C12P 21/06 | (2006.01) | |
| C12P 21/04 | (2006.01) | |
| C12N 9/04 | (2006.01) | |
| C12N 1/20 | (2006.01) | |
| C12N 15/00 | (2006.01) | |
| C12Q 1/68 | (2006.01) | |
| C12Q 1/20 | (2006.01) | |
| C07H 21/04 | (2006.01) | |

(52) U.S. Cl.
USPC ............... 435/132; 435/4; 435/6.1; 435/440; 435/252.3; 435/320.1; 435/69.1; 435/71.1; 435/190; 536/23.2

(58) Field of Classification Search
None
See application file for complete search history.

(56) References Cited

U.S. PATENT DOCUMENTS
2006/0211099 A1  9/2006  Althöfer et al.
2007/0083055 A1  4/2007  Sturmer et al.

FOREIGN PATENT DOCUMENTS
| | | |
|---|---|---|
| EP | 0 273 658 B1 | 10/1990 |
| EP | 1 152 054 A1 | 11/2001 |
| WO | WO-2004/090094 A2 | 10/2004 |
| WO | WO-2005/033094 A2 | 4/2005 |
| WO | WO-2005/108590 A2 | 11/2005 |

OTHER PUBLICATIONS

Branden et al. Introduction to Protein Structure, Garland Publishing Inc., New York, p. 247, 1991.*
Althofer et al. Raw Machine Translation of WO 2004/090094 A2 retrieved from http://ep.espacenet.com/?locale=EN_ep on Mar. 24, 2010.*
Liu, H., et al., "Chemo-enzymatic synthesis of the antidepressant duloxetine and its enantiomer", Chirality, 2000, vol. 12, pp. 26-29.
Soni, P., et al., "Biotransformations for the productionof the chiral drug (S)-duloxetine catalyzed by a novel isolate of *Candida tropicalis*", Appl. Microbiol. Biotechnol., 2005, vol. 67, pp. 771-777.

* cited by examiner

*Primary Examiner* — Yong Pak
(74) *Attorney, Agent, or Firm* — Novak Druce Connolly Bove + Quigg LLP

(57) ABSTRACT

The present invention relates to proteins having an enzymatic activity of reducing substituted alkanones such as 3-methylamino-1-(2-thienyl)-propan-1-one. The invention furthermore relates to nucleic acids coding for said proteins, nucleic acid constructs, vectors, genetically modified microorganisms and to methods for preparing optically active substituted alkanols, such as, for example, (S)-3-methylamino-1-(2-thienyl)-(S)-propanol.

10 Claims, No Drawings

DEHYDROGENASES, THE DERIVATIVES THEREOF, AND METHOD FOR THE PRODUCTION OF OPTICALLY ACTIVE ALKANOLS

RELATED APPLICATIONS

This application is a national stage application under 35 U.S.C. 371 of PCT/EP2006/066336, filed Sep. 14, 2006, which claims benefit of German application 102005044736.8, filed Sep. 19, 2005.

SUBMISSION OF SEQUENCE LISTING

The Sequence Listing associated with this application is filed in electronic format via EFS-Web and hereby incorporated by reference into the specification in its entirety. The name of the text file containing the Sequence Listing is Revised_Sequence_List_12810_00628_US.

The present invention relates to proteins having an enzymatic activity for reducing substituted alkanones such as 3-methylamino-1-(2-thienyl)-propan-1-one. The invention furthermore relates to nucleic acids coding for said proteins, nucleic acid constructs, vectors, genetically modified microorganisms and to methods for preparing optically active substituted alkanols, in particular (S)-alkanols, such as, for example, (S)-3-methylamino-1-(2-thienyl)-(S)-propanol.

PRIOR ART

Dehydrogenases are versatile catalysts for the enantioselective reduction of aldehydes or ketones to give the corresponding alcohols. A distinction is made between (R)- and (S)-specific dehydrogenases. These catalysts are increasingly being used for industrial synthesis of optically active alcohols. Optical activity is the precondition of selective action of many pharmaceutical and agrochemical active compounds. Here, one enantiomer may have the desired action and the other enantiomer a genotoxic action. For this reason, synthesis of pharmaceutical and agrochemical active compounds employs catalysts having the required stereospecificity for preparing optically active alcohols.

3-Methylamino-1-(2-thienyl)-(S)-propanol ("Duloxetine alcohol") is a building block in Duloxetine synthesis. Duloxetine is a pharmaceutical active compound which is currently going through the approval process and is intended to be used in the fields of indication of depression and incontinence.

Synthesis routes to Duloxetine alcohol and Duloxetine are described in the literature (cf. EP-A-0 273 658). These synthesis routes have the disadvantage that the synthesis results in a racemic alcohol mixture, requiring subsequent resolution of the racemate byating the racemconverte into a mixture of diastereomers via formation of a salt with an optically active counterion. The diastereomers are then physically separated. This results in high process costs, due to repeated separation of solids and liquids, and increased use of starting compounds, due to addition of an optically active salt for separation.

Stereospecific reduction of 3-methylamino-1-(2-thienyl)-propanone would provide a less expensive path to Duloxetine alcohol.

EP1152054 describes new carbonyl reductases and the use thereof for preparing tert-butyl(3R,5S)-6-chloro-3,5-dihydroxyhexanoate.

WO 04/90094 describes carnitine dehydrogenases and the use thereof for preparing optically active alkanols.

BRIEF DESCRIPTION OF THE INVENTION

It is an object of the present invention to find a route to stereospecific reduction of substituted alkanones such as 3-methylamino-1-(2-thienyl)-propan-2-one.

We have found that this object is achieved by providing new dehydrogenases which are capable of catalyzing the above reaction in a stereospecific manner.

Firstly, the invention relates to a method for microbiological, in particular enantioselective, preparation of substituted alkanols of the formula I

(I)

in which n is an integer from 0 to 5, in particular 0, 1 or 2;

Cyc is an optionally substituted, mono- or polynuclear, saturated or unsaturated, carbocyclic or heterocyclic ring, in particular an optionally substituted, unsaturated, mononuclear heterocyclic ring, and $R^1$ is halogen, SH, OH, $NO_2$, $NR^2R^3$ or $NR^2R^3R^{4+}X^-$, in particular halogen or $NR^2R^3$, where $R^2$, $R^3$ and $R^4$ independently of one another are H or a lower alkyl or lower alkoxy radical and $X^-$ is a counterion, wherein, in a medium comprising an alkanone of the formula II

(II)

in which n, Cyc and $R^1$ are as defined above, a) a microorganism producing a dehydrogenase having the polypeptide SEQ ID NO: 2 or NO: 4, or having a polypeptide sequence in which up to 25% of the amino acid residues have been altered by deletion, insertion, substitution or a combination thereof, compared to SEQ ID NO: 2 or NO: 4 is cultured, or b) a dehydrogenase as mentioned under a) is incubated, the compound of the formula II being enzymatically reduced to give the compound of the formula I, and the essentially enantiomerically pure product formed is isolated.

In a particularly preferred embodiment, the method serves to prepare 3-methylamino-1-(2-thienyl)-(S)-propanol of the formula III

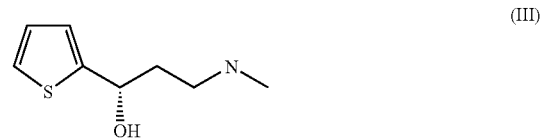

(III)

wherein, in a medium comprising 3-methylamino-1-(2-thienyl)-propan-2-one of the formula IV

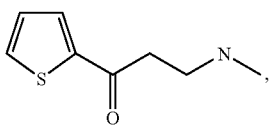
(IV)

said compound is enzymatically reduced to give a compound of the formula III and the essentially enantiomerically pure product formed is isolated.

Preference is given to using in these methods an enzyme having a polypeptide sequence according to SEQ ID NO: 2 or NO: 4.

Enzymes of this kind may be isolated for example from microorganisms of the genus *Candida*.

In a particularly preferred embodiment of the invention, the enzyme is selected from among enzymes comprising an amino acid sequence according to SEQ ID NO: 2, 4 or encoded by nucleic acid sequences derived therefrom; and functional equivalents of said enzymes, which have dehydrogenase activity and catalyze the enantioselective synthesis of a compound of the formula I.

For example, the enzyme having dehydrogenase activity may be encoded by a nucleic acid sequence according to SEQ ID NO:1 or NO: 3 or a functional equivalent thereof.

Preference is given to carrying out the method of the invention with addition of reduction equivalents (NADH or NADPH) or under (biochemical or electrochemical) conditions under which the reduction equivalents consumed in the reaction are regenerated.

Furthermore, preference is given to allowing the compound of the formula II, for example of the formula IV, to be reacted in the presence of a microorganism selected from among bacteria of the families Enterobacteriaceae, Pseudomonadaceae, Rhizobiaceae, Streptomycetaceae and Nocardiaceae. Said microorganism may in particular be a recombinant microorganism which has been transformed with a nucleic acid construct coding for an inventive enzyme having dehydrogenase activity as defined above.

In particular, the invention relates to a method as defined above, wherein a) a microorganism producing an enzyme having dehydrogenase activity is isolated from a natural source or is prepared recombinantly, b) said microorganism is propagated, c) said enzyme having dehydrogenase activity is, if appropriate, isolated from said microorganism or a protein fraction comprising said enzyme is prepared from said microorganism, and d) said microorganism according to stage b) or said enzyme according to stage c) is transferred into a medium comprising a compound of the formula I.

The invention furthermore relates to a compound of the formula V

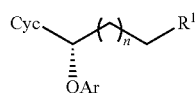
(V)

in which n, Cyc and R¹ are as defined above and Ar is a mono- or polynuclear, optionally substituted aryl radical, and wherein a) first a compound of the formula I is prepared microbiologically as defined in any of the preceding claims; and b) the compound of the formula I is reacted with an aromatic compound of the formula VI Ar—Y (VI)

in which Ar is as defined above and Y is a leaving group, and c) the compound of the formula V is isolated and, if appropriate, converted to a pharmaceutically acceptable acid addition salt such as oxalates, for example.

Preference is given here to preparing a compound of the formula V in which Ar is 1-naphthyl, Cyc is 2-thienyl, R¹ is monomethylamino and n is 1.

The invention further relates to polypeptides which comprise an amino acid sequence according to SEQ ID NO: 2 or 4 or are encoded by nucleic acid sequences derived therefrom; and to functional equivalents of these enzymes, which have dehydrogenase activity and which catalyze the enantioselective synthesis of a compound of the formula I and/or III.

The invention moreover relates to coding nucleic acid sequences comprising the sequence coding for a polypeptide as defined above.

The invention furthermore relates to expression cassettes comprising a coding nucleic acid sequence as defined above and operatively linked to at least one regulatory nucleic acid sequence.

The invention further relates to recombinant vectors comprising at least one such expression cassette.

The invention also relates to prokaryotic or eukaryotic hosts transformed with at least one vector of the invention.

Finally, the invention relates to the use of an enzyme having dehydrogenase activity as defined above or of a microorganism producing said enzyme for preparing compounds of the formula I or III, in particular for preparing Duloxetine of the formula VII

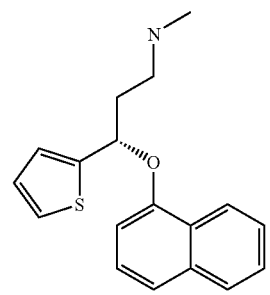
(VII)

DETAILED DESCRIPTION OF THE INVENTION

A. General Terms and Definitions

Unless specified otherwise, the following general meanings apply:

"Halogen" is fluorine, chlorine, bromine or iodine, in particular fluorine or chlorine.

"Lower alkyl" is straight-chain or branched alkyl radicals having 1 to 6 carbon atoms, such as methyl, ethyl, isopropyl or n-propyl, n-butyl, isobutyl, sec- or tert-butyl, n-pentyl or 2-methylbutyl, n-hexyl, 2-methylpentyl, 3-methylpentyl, 2-ethylbutyl.

"Lower alkenyl" is the mono- or polyunsaturated, preferred mono- or diunsaturated, analogs of the abovementioned alkyl radicals having 2 to 6 carbon atoms, it being possible for the double bond to be in any position of the carbon chain.

"Lower alkoxy" is the oxygen-terminated analogs of the above alkyl radicals.

"Aryl" is a mono- or polynuclear, preferably mono- or binuclear, optionally substituted aromatic radical, in particular phenyl or a naphthyl bound via any ring position, such as 1- or 2-naphthyl. If appropriate, these aryl radicals may carry 1 or 2 identical or different substituents selected from among halogen, lower alkyl, lower alkoxy as defined above or trifluoromethyl.

B. Substituted Alkanones, (S)-Alkanols and Derivatives Thereof

Alkanols accessible by enzymatic catalysis according to the invention are those of the above formula (I) in which
n is an integer from 0 to 5;
Cyc is an optionally substituted, mono- or polynuclear, saturated or unsaturated, carbocyclic or heterocyclic ring, and
$R^1$ is halogen, SH, OH, $NO_2$, $NR^2R^3$ or $NR^2R^3R^{4+}X^-$, where $R^2$, $R^3$ and $R^4$ independently of one another are H or a lower alkyl or lower alkoxy radical and $X^-$ is a counterion.

The alkanols of the above formula II, used for enzymatic synthesis, are compounds known per se and obtainable with application of well-known organic synthesis methods (cf. e.g. EP-A-0 273 658).

In the above compounds, n is preferably 0, 1 or 2, in particular 1.

Examples of carbo- and heterocyclic groups Cyc which should be mentioned are in particular mono- or binuclear, preferably mononuclear, groups having up to 4, preferably 1 or 2, identical or different ring heteroatoms selected from among O, N and S:

Said carbo- or heterocyclic rings comprise in particular from 3 to 12, preferably 4, 5 or 6, ring carbon atoms. Examples which may be mentioned are cyclopropyl, cyclobutyl, cyclopentyl, cyclohexyl, cycloheptyl, the mono- or polyunsaturated analogs thereof such as cyclobutenyl, cyclopentenyl, cyclohexenyl, cycloheptenyl, cyclohexadienyl, cycloheptadienyl; and also 5- to 7-membered saturated or mono- or polyunsaturated heterocyclic radicals having from 1 to 4 heteroatoms selected from among O, N and S, it being possible for the heterocycle to be fused to another heterocycle or carbocycle, if appropriate. Radicals which should be mentioned here are in particular radicals derived from pyrrolidine, tetrahydrofuran, piperidine, morpholine, pyrrole, furan, thiophene, pyrazole, imidazole, oxazole, thiazole, pyridine, pyran, pyrimidine, pyridazine, pyrazine, coumarone, indole and quinoline.

The radicals Cyc may be bound here via any ring position, preferably via a ring carbon atom, to the alkanone or the alkanol.

Examples of suitable Cyc radicals are 2-thienyl, 3-thienyl; 2-furanyl, 3-furanyl; 2-pyridyl, 3-pyridyl or 4-pyridyl; 2-thiazolyl, 4-thiazolyl or 5-thiazolyl; 4-methyl-2-thienyl, 3-ethyl-2-thienyl, 2-methyl-3-thienyl, 4-propyl-3-thienyl, 5-n-butyl-2-thienyl, 4-methyl-3-thienyl, 3-methyl-2-thienyl; 3-chloro-2-thienyl, 4-bromo-3-thienyl, 2-iodo-3-thienyl, 5-iodo-3-thienyl, 4-fluoro-2-thienyl, 2-bromo-3-thienyl and 4-chloro-2-thienyl.

The radicals Cyc may furthermore be mono- or polysubstituted, for example mono- or disubstituted. The substituents are preferably located on a ring carbon atom. Examples of suitable substituents are halogen, lower alkyl, lower alkenyl, lower alkoxy, —OH, —SH, —$NO_2$ or $NR^2R^3$, where $R^2$ and $R^3$ are as defined above, preferably halogen or lower alkyl.

$R^1$ is in particular halogen, $NR^2R^3$ or $NR^2R^3R^{4+}X^-$, where $R^2$, $R^3$ or $R^2$, $R^3$ and $R^4$ are independently of one another H or a lower alkyl or lower alkoxy radical and $X^-$ is a counterion, any of the radicals $R^2$, $R^3$ and $R^4$ being preferably H. Examples of suitable counterions are acid anions as obtained, for example, from preparation of an acid addition salt. Examples thereof are mentioned, for example, in EP-A-0 273 658 which is hereby incorporated by reference. Preferred examples of radicals $R^1$ are in particular fluorine or chlorine and also $NR^2R^3$ in which $R^2$ and $R^3$ are identical or different and are H or methyl, ethyl or n-propyl; particularly preferably, $R^1$ is chlorine or —NHmethyl.

C. Enzymes Having Dehydrogenase Activity

The inventive enzymes having dehydrogenase activity can be found in microorganisms of the Genus *Candida*. The enzyme or enzymes have a high enzymatic activity for reducing alkanones of the formula II, such as 3-methylamino-1-(2-thienyl)-propan-1-one to 3-methylamino-1-(2-thienyl)-(S)-propanol. The dehydrogenase likewise converts other substrates such as, for example, the dimethyl derivatives of the ketone as well as the monomethyl compounds.

Preferably, but without being limited thereto, enzymes of this kind can be obtained from microorganisms of the genera *Candida*, in particular of the species *C. magnoliae*.

Preferred enzymes having dehydrogenase activity comprise an amino acid sequence according to SEQ ID NO: 2 or 4 or an amino acid sequence in which up to 25%, preferably up to 20%, particularly preferably up to 10%, in particular up to 8, 6, 5, 4, 3, 2, and 1%, of the amino acid residues have been altered by deletion, insertion, substitution or a combination thereof, compared to SEQ ID NO:2 or NO: 4.

Particular preference is given to those of the abovementioned dehydrogenases, which have a Thr residue in position 2 or a Gly residue in position 12.

The invention likewise comprises "functional equivalents" of the specifically disclosed enzymes having dehydrogenase activity and the use of these in the methods of the invention.

"Functional equivalents" or analogs of the specifically disclosed enzymes are, for the purposes of the present invention, polypeptides which differ from said enzymes but still retain the desired biological activity such as substrate specificity, for example. Thus, for example, "functional equivalents" mean enzymes which reduce 3-methylamino-1-(2-thienyl)-propan-1-one to the corresponding S-alcohol and which have at least 50%, preferably 75%, particularly preferably 85%, of the activity of an enzyme comprising any of the amino acid sequences listed under SEQ ID NO:2 or 4. Moreover, functional equivalents are preferably stable between pH 4 and 10 and advantageously have a pH optimum of between pH 5 and 8 and a temperature optimum in the range from 20° C. to 80° C.

"Functional equivalents" mean according to the invention in particular also mutants which have in at least one sequence position of the abovementioned amino acid sequences an amino acid different from the specifically mentioned amino acids but which have nevertheless one of the abovementioned biological activities. "Functional equivalents" thus comprise the mutants obtainable by one or more amino acid additions, substitutions, deletions and/or inversions, it being possible for said modifications to occur in any sequence position as long as they result in a mutant having the property profile of the invention. In particular, functional equivalence also exists when the reactivity patterns between mutant and unmodified polypeptide correspond qualitatively, i.e. when identical substrates are converted at different rates, for example.

"Functional equivalents" in the above sense are also "precursors" of the polypeptides described and also "functional derivatives" and "salts" of said polypeptides.

In this context, "precursors" are natural or synthetic precursors of the polypeptides with or without the desired biological activity.

The term "salts" means not only salts of carboxyl groups, but also acid addition salts of amino groups of the protein molecules of the invention. Salts of carboxyl groups can be prepared in a manner known per se and comprise inorganic salts such as, for example, sodium, calcium, ammonium, iron and zinc salts, and also salts with organic bases such as, for example, amines, such as triethanolamine, arginine, lysine, piperidine, and the like. The invention likewise relates to acid addition salts such as, for example, salts with mineral acids such as hydrochloric acid or sulfuric acid and salts with organic acids such as acetic acid and oxalic acid.

"Functional derivatives" of polypeptides of the invention may likewise be prepared on functional amino acid side groups or the N- or C-terminal end thereof with the aid of known techniques. Derivatives of this kind comprise, for example, aliphatic esters of carboxylic acid groups, amides of carboxylic acid groups, obtainable by reaction with ammonia or with a primary or secondary amine; N-acyl derivative of free amino groups, prepared by reaction with acyl groups; or O-acyl derivatives of free hydroxyl groups, prepared by reaction with acyl groups.

"Functional equivalents" also comprise, of course, polypeptides obtainable from other organisms and also naturally occurring variants. For example, regions of homologous sequences can be determined by sequence comparison, and equivalent enzymes can be established on the basis of the specific requirements of the invention.

"Functional equivalents" likewise comprise fragments, preferably individual domains or sequence motifs, of the polypeptides of the invention, which have the desired biological function, for example.

Moreover, "functional equivalents" are fusion proteins which have any of the abovementioned polypeptide sequences or functional equivalents derived therefrom and at least one other heterologous sequence functionally different therefrom in functional N- or C-terminal linkage (i.e. without substantial mutual functional impairment of the fusion protein moieties). Nonlimiting examples of heterologous sequences of this kind are signal peptides or enzymes, for example.

The invention also relates to "functional equivalents" which are homologs of the specifically disclosed proteins. These have at least 75%, preferably at least 80%, in particular at least 85%, such as, for example, 90%, 95% or 99%, homology to any of the specifically disclosed amino acid sequences, calculated by the algorithm of Pearson and Lipman, Proc. Natl. Acad, Sci. (USA) 85(8), 1988, 2444-2448. Percentage homology of a homologous polypeptide of the invention means in particular percentage identity of the amino acid residues based on the total length of one of the amino acid sequences specifically described herein.

In the event of a possible protein glycosylation, "functional equivalents" of the invention comprise proteins of the above-specified type in deglycosylated or glycosylated form and also modified forms obtainable by altering the glycosylation pattern.

Homologs of the proteins or polypeptides of the invention may be generated by mutagenesis, for example by point mutation or truncation of the protein.

Homologs of the proteins of the invention may be identified by screening combinatorial libraries of mutants such as truncation mutants, for example. For example, it is possible to generate a variegated library of protein variants by combinatorial mutagenesis at the nucleic acid level, for example by enzymatically ligating a mixture of synthetic oligonucleotides. There is a multiplicity of methods which can be used to prepare libraries of potential homologs from a degenerate oligonucleotide sequence. Chemical synthesis of a degenerate gene sequence may be carried out in a DNA synthesizer, and the synthetic gene can then be ligated into a suitable expression vector. The use of a degenerate set of genes makes it possible to provide, in one mixture, all sequences which encode the desired set of potential protein sequences. Methods for synthesizing degenerate oligonucleotides are known to the skilled worker (e.g. Narang, S. A. (1983) Tetrahedron 39:3; Itakura et al. (1984) Annu. Rev. Biochem. 53:323; Itakura et al., (1984) Science 198:1056; Ike et al. (1983) Nucleic Acids Res. 11:477).

The prior art discloses a plurality of techniques for screening gene products of combinatorial libraries which have been prepared by point mutations or truncation and for screening cDNA libraries for gene products with a selected property. These techniques can be adapted to the rapid screening of the gene libraries which have been generated by combinatorial mutagenesis of homologs of the invention. The most frequently used techniques for screening large gene libraries subjected to high-throughput analysis comprise cloning of the gene library into replicable expression vectors, transforming suitable cells with the resulting vector library and expressing the combinatorial genes under conditions under which detection of the desired activity facilitates isolation of the vector encoding the gene whose product has been detected. Recursive ensemble mutagenesis (REM), a technique which increases the frequency of functional mutants in the libraries, may be used in combination with the screening assays in order to identify homologs (Arkin and Yourvan (1992) PNAS 89:7811-7815; Delgrave et al. (1993) Protein Engineering 6(3):327-331).

D. Coding Nucleic Acid Sequences

In the context of the present invention, the terms "to express" or "overexpression" describe production of or increase in intracellular activity of one or more enzymes in a microorganism, which are encoded by the corresponding DNA. For this purpose, for example, it is possible to introduce a gene into an organism, to replace an existing gene with a different gene, to increase the copy number of the gene or genes, to use a strong promoter or to use a gene coding for a corresponding enzyme having a high activity, and it is possible to combine these measures, if appropriate.

The invention relates in particular to nucleic acid sequences coding for an enzyme having dehydrogenase activity. Preference is given to nucleic acid sequences comprising a sequence according to SEQ ID NO:1 or NO: 3. All of the nucleic acid sequences mentioned herein (single- and double-strand DNA and RNA sequences such as, for example, cDNA and mRNA) can be prepared from the nucleotide building blocks in a manner known per se by chemical synthesis, such as, for example, by fragment condensation of individual overlapping, complementary nucleic acid building blocks of the double helix. Oligonucleotides may be chemically synthesized, for example, in a known manner, by the phosphoramidite method (Voet, Voet, 2nd Edition, Wiley Press New York, pages 896897). Annealing synthetic oligonucleotides and filling in gaps with the aid of the Klenow fragment of DNA polymerase, and ligation reactions and also general cloning methods are described in Sambrook et al. (1989), Molecular Cloning: A laboratory manual, Cold Spring Harbor Laboratory Press.

The invention also relates to nucleic acid sequences (single- and double-stranded DNA and RNA sequences such as cDNA and mRNA, for example) encoding any of the above polypeptides and their functional equivalents which are obtainable, for example, by using artificial nucleotide analogs.

The invention relates to both isolated nucleic acid molecules coding for polypeptides or proteins of the invention or for biologically active segments thereof and nucleic acid fragments which may be used, for example, for use as hybridization probes or primers for identifying or amplifying coding nucleic acids of the invention.

The nucleic acid molecules of the invention may moreover contain untranslated sequences of the 3'- and/or 5'-end of the coding region of the gene.

The invention furthermore comprises the nucleic acid molecules complementary to the specifically described nucleotide sequences or a section of said nucleic acid molecules.

The nucleotide sequences of the invention make possible the generation of probes and primers which can be used for identifying and/or cloning homologous sequences in other cell types and organisms. Such probes and primers usually comprise a nucleotide sequence region which hybridizes under "stringent" conditions (see hereinbelow) to at least about 12, preferably at least about 25, such as, for example, about 40, 50 or 75, consecutive nucleotides of a sense strand of a nucleic acid sequence of the invention or of a corresponding antisense strand.

An "isolated" nucleic acid molecule is removed from other nucleic acid molecules present in the natural source of the nucleic acid and may, in addition, be essentially free of other cellular materials or culture medium, if produced by recombinant techniques, or free of chemical precursors or other chemicals, if chemically synthesized.

A nucleic acid molecule of the invention may be isolated by means of standard techniques of molecular biology and the sequence information provided according to the invention. For example, cDNA can be isolated from a suitable cDNA library by using any of the specifically disclosed complete sequences or a section thereof as hybridization probe and standard hybridization techniques (as described, for example, in Sambrook, J., Fritsch, E. F. and Maniatis, T. Molecular Cloning: A Laboratory Manual. 2nd Ed., Cold Spring Harbor Laboratory, Cold Spring Harbor Laboratory Press, Cold Spring Harbor, N.Y., 1989). In addition, a nucleic acid molecule comprising any of the disclosed sequences or a section thereof can be isolated by polymerase chain reaction using the oligonucleotide primers generated on the basis of said sequence. The nucleic acid amplified in this way may be cloned into a suitable vector and characterized by DNA sequence analysis. The oligonucleotides of the invention may furthermore be prepared by standard methods of synthesis, for example using a DNA synthesizer.

The nucleic acid sequences of the invention can be identified and isolated in principle from all organisms. Advantageously, the nucleic acid sequences of the invention, such as SEQ ID NO: 1 or No: 3, can be isolated from microorganisms of the genus *Candida*.

Nucleic acid sequences of the invention, such as SEQ ID NO: 1 or NO: 3 derivatives thereof, homologs or parts of the sequences, can be isolated from other fungi or bacteria, for example via genomic or cDNA libraries, by using, for example, common hybridization methods or the PCR technique. These DNA sequences hybridize with the sequences of the invention under standard conditions. For hybridization, it is advantageous to use short oligonucleotides of the conserved regions, for example of the active site, which can be identified via comparisons with L-carnitine dehydrogenase in a manner known to the skilled worker. However, it is also possible to use longer fragments of the nucleic acids of the present invention or the complete sequences for the hybridization. Said standard conditions vary depending on the nucleic acid used (oligonucleotide, longer fragment or complete sequence) or depending on the type of nucleic acids, DNA or RNA, being used for hybridization. Thus, for example, the melting temperatures of DNA:DNA hybrids are approx. 10° C. lower than those of DNA:RNA hybrids of the same length.

Standard conditions mean, for example, depending on the nucleic acid, temperatures between 42 and 58° C. in an aqueous buffer solution at a concentration of between 0.1 and 5×SSC (1×SSC=0.15 M NaCl, 15 mM sodium citrate, pH 7.2) or additionally in the presence of 50% formamide, for example 42° C. in 5×SSC, 50% formamide, The hybridization conditions for DNA:DNA hybrids are advantageously 0.1×SSC and temperatures between about 20° C. and 45° C., preferably between about 30° C. and 45° C. The hybridization conditions for DNA:RNA hybrids are advantageously 0.1× SSC and temperatures between about 30° C. and 55° C., preferably between about 45° C. and 55° C. These hybridization temperatures indicated are melting temperatures calculated by way of example for a nucleic acid of approx. 100 nucleotides in length and having a G+C content of 50% in the absence of formamide. The experimental conditions for DNA hybridization are described in relevant genetics textbooks, such as, for example, Sambrook et al., "Molecular Cloning", Cold Spring Harbor Laboratory, 1989, and can be calculated using formulae known to the skilled worker, for example as a function of the length of the nucleic acids, the type of hybrid or the G+C content. Further information on hybridization can be found by the skilled worker in the following textbooks: Ausubel et al. (eds), 1985, Current Protocols in Molecular Biology, John Wiley & Sons, New York; Hames and Higgins (eds), 1985, Nucleic Acids Hybridization: A Practical Approach, IRL Press at Oxford University Press, Oxford; Brown (ed), 1991, Essential Molecular Biology: A Practical Approach, IRL Press at Oxford University Press, Oxford.

The invention also relates to derivatives of the specifically disclosed or derivable nucleic acid sequences.

Thus it is possible for further nucleic acid sequences of the invention to be derived, for example, from SEQ ID NO:1 or NO: 3 and to differ therefrom by addition, substitution, insertion or deletion of one or more nucleotides, while still coding for polypeptides with the desired property profile.

The invention also comprises those nucleic acid sequences which comprise "silent mutations" or which are modified, in comparison with a specifically mentioned sequence, according to the codon usage of a specific source organism or host organism, and also naturally occurring variants thereof, such as splice variants or allelic variants, for example.

The invention also relates to sequences obtainable by conservative nucleotide substitutions (i.e. the amino acid in question is replaced with an amino acid of the same charge, size, polarity and/or solubility).

The invention also relates to the molecules derived from the specifically disclosed nucleic acids by way of sequence polymorphisms. These genetic polymorphisms may exist between individuals within a population, owing to natural variations. These natural variations usually cause a variance of from 1 to 5% in the nucleotide sequence of a gene.

Derivatives of the inventive nucleic acid sequence having the sequence SEQ ID NO: 1 or NO: 3 mean, for example, allelic variants having at least 40% homology at the deduced amino acid level, preferably at least 60% homology, very particularly preferably at least 80% homology, over the entire sequence region (with regard to homology at the amino acid level, reference may be made to the above comments regarding polypeptides). Advantageously, the homologies may be higher across parts of the sequence.

Furthermore, derivatives also mean homologs of the nucleic acid sequences of the invention, in particular of SEQ ID NO: 1 or NO: 3, for example fungal or bacterial homologs, truncated sequences, single-stranded DNA or RNA of the coding or noncoding DNA sequence. Thus, for example, homologs of SEQ ID NO: 1 at the DNA level are at least 40%, preferably at least 60%, particularly preferably at least 70%, very particularly preferably at least 80%, homologous over the entire DNA region indicated in SEQ ID NO: 1.

Moreover, derivatives mean, for example, fusions with promoters. Said promoters which are located upstream of the nucleotide sequences may have been modified by one or more nucleotide substitutions, insertions, inversions and/or deletions, without adversely affecting the functionality or efficacy of the said promoters, however. Furthermore, the efficacy of said promoters may be increased by modifying their sequence, or said promoters may be replaced completely with more efficient promoters, including those of organisms of different species.

Derivatives also mean variants whose nucleotide sequence in the region of from −1 to −1000 bases upstream of the start codon or from 0 to 1000 bases downstream of the stop codon has been altered so as to modify, preferably increase, gene expression and/or protein expression.

Furthermore, the invention also comprises nucleic acid sequences which hybridize with the abovementioned coding sequences under "stringent conditions". These polynucleotides can be identified when screening genomic or cDNA libraries and, if appropriate, be amplified therefrom by means of PCR using suitable primers and subsequently isolated using suitable probes, for example. In addition, polynucleotides of the invention may also be synthesized chemically. This property means the ability of a poly- or oligonucleotide to bind under stringent conditions to a virtually complementary sequence, while there are no nonspecific bindings between noncomplementary partners under these conditions. For this purpose, the sequences should be 70-100%, preferably 90-100%, complementary. The property of complementary sequences of being able to bind specifically to one another is exploited, for example, in the Northern or Southern blot technique or for primer binding in PCR or RT-PCR. For this purpose, oligonucleotides from a length of 30 base pairs are customarily used. Stringent conditions mean, for example in the Northern blot technique, using a washing solution, for example 0.1×SSC buffer containing 0.1% SDS (20×SSC: 3M NaCl, 0.3M sodium citrate, pH 7.0) at a temperature of 50-70° C., preferably 60-65° C., for eluting nonspecifically hybridized cDNA probes or oligonucleotides. In the process, only highly complementary nucleic acids remain bound to one another, as mentioned above. Setting of stringent conditions is known to the skilled worker and described, for example, in Ausubel et al., Current Protocols in Molecular Biology, John Wiley & Sons, N.Y. (1989), 6.3.1-6.3.6.

E. Constructs of the Invention

The invention moreover relates to expression constructs comprising, under the genetic control of regulatory nucleic acid sequences, a nucleic acid sequence coding for a polypeptide of the invention; and also to vectors comprising at least one of said expression constructs.

Such constructs of the invention preferably comprise a promoter 5' upstream of the particular coding sequence and a terminator sequence 3' downstream and also, if appropriate, further common regulatory elements, in each case operatively linked to the coding sequence.

An "operative linkage" means the sequential arrangement of promoter, coding sequence, terminator and, if appropriate, further regulatory elements in such a way that each of said regulatory elements is able to carry out its function in expression of the coding sequence. Examples of operatively linkable sequences are targeting sequences and also enhancers, polyadenylation signals, and the like. Other regulatory elements comprise selectable markers, amplification signals, origins of replications, and the like. Suitable regulatory sequences are described, for example, in Goeddel, Gene Expression Technology Methods in Enzymology 185, Academic Press, San Diego, Calif. (1990).

A nucleic acid construct of the invention means in particular the dehydrogenase genes having the sequence SEQ ID NO: 1 and NO: 3 and the derivatives and homologs thereof, which advantageously have been operatively or functionally linked to one or more regulatory signals for controlling, for example increasing, gene expression.

In addition to these regulatory sequences, the natural regulation of said sequences may still be present upstream of the actual structural genes and, if appropriate, may have been genetically modified so that natural regulation has been switched off and expression of the genes has been increased. However, construction of the nucleic acid construct may also be simpler, i.e. no additional regulatory signals have been inserted upstream of the coding sequence (such as, for example, SEQ ID NO: 1 or No: 3 or its homologs), and the natural promoter together with its regulation has not been removed. Instead, the natural regulatory sequence has been mutated in such as way that regulations no longer takes place and gene expression is increased.

A preferred nucleic acid construct advantageously also comprises one or more of the already mentioned enhancer sequences, functionally linked to the promoter, which enable expression of the nucleic acid sequence to be increased. Additional advantageous sequences such as further regulatory elements or terminators may also be inserted at the 3' end of the DNA sequences. One or more copies of the nucleic acids of the invention may be comprised in the construct. The construct may also comprise other markers such as resistances to antibiotics or auxotrophy-complementing genes, if appropriate, for selection for the construct.

Advantageous regulatory sequences for the method of the invention are present, for example, in promoters such as cos, tac, trp, tet, trp-tet, lpp, lac, lpp-lac, lacI$^q$, T7, T5, T3, gal, trc, ara, rhaP (rhaP$_{BAD}$)SP6, lambda-P$_R$ or in the lambda-P$_L$ promoter, which are advantageously used in Gram-negative bacteria. Other advantageous regulatory sequences are comprised, for example, in the Gram-positive promoters amy and SPO2, in the yeast or fungal promoters ADC1, MFalpha, AC, P-60, CYC1, GAPDH, TEF, rp28, ADH. In this connection, the promoters of pyruvate decarboxylase and of methanol oxidase, for example from *Hansenula*, are also advantageous. It is also possible to use artificial promoters for regulation.

The nucleic acid construct is advantageously expressed in a host organism by inserting it into a vector such as a plasmid or a phage, for example, which makes possible optimal expression of the genes in the host. Vectors mean, apart from plasmids and phages, also any other vectors known to the skilled worker, i.e., for example, viruses such as SV40, CMV, Baculovirus and Adenovirus, Transposons, IS elements, plasmids, cosmids, and linear or circular DNA. These vectors can be replicated autonomously in the host organism or chromosomally. These vectors constitute a further embodiment of the invention. Suitable plasmids are, for example, in *E. coli* pLG338, pACYC184, pBR322, pUC18, pUC19, pKC30, pRep4, pHS1, pKK223-3, pDHE19.2, pHS2, pPLc236, pMBL24, pLG200, pUR290, pIN-III[113]-B1, □gt11 or pBdCl, in *Streptomyces* pIJ101, pIJ364, pIJ702 or pIJ361, in *Bacillus* pUB110, pC194 or pBD214, in *Corynebacterium* pSA77 or pAJ667, in fungi pALS1, pIL2 or pBB116, in yeasts 2alphaM, pAG-1, YEp6, YEp13 or pEMBLYe23 or in plants pLGV23, pGHlac+, pBIN19, pAK2004 or pDH51. The plasmids mentioned are a small selection of possible plasmids. Other plasmids are well known to the skilled worker and can be found, for example, in the book Cloning Vectors (Eds. Pouwels P. H. et al. Elsevier, Amsterdam-New York-Oxford, 1985, ISBN 0 444 904018).

For expression of the further genes which are comprised, the nucleic acid construct advantageously additionally comprises 3'- and/or 5'-terminal regulatory sequences for enhancing expression, which are selected for optimal expression depending on the host organism and the gene or genes selected.

These regulatory sequences are intended to make possible specific expression of the genes and protein expression. Depending on the host organism, this may mean, for example, that the gene is expressed or overexpressed only after induction or that it is immediately expressed and/or overexpressed.

The regulatory sequences or factors may preferably have a positive effect on, and thus increase, gene expression of the genes introduced. Thus, the regulatory elements can advantageously be enhanced at the transcriptional level by using strong transcription signals such as promoters and/or enhancers. However, in addition it is also possible to enhance translation by improving, for example, stability of the mRNA.

In a further embodiment of the vector, the vector comprising the nucleic acid construct of the invention or the nucleic acid of the invention may advantageously also be introduced into the microorganisms in the form of a linear DNA and integrated via heterologous or homologous recombination into the genome of the host organism. This linear DNA may consist of a linearized vector such as a plasmid or only of the nucleic acid construct or the nucleic acid of the invention.

It is advantageous for optimal expression of heterologous genes in organisms to modify the nucleic acid sequences according to the specific codon usage used in the organism. The codon usage can be readily determined on the basis of computer evaluations of other, known genes of the organism in question.

The expression cassette of the invention is prepared by fusing a suitable promoter to a suitable coding nucleotide sequence and a terminator signal or polyadenylation signal. For this purpose, conventional recombination and cloning techniques are used, as are described, for example, in T. Maniatis, E. F. Fritsch and J. Sambrook, Molecular Cloning: A Laboratory Manual, Cold Spring Harbor Laboratory, Cold Spring Harbor, N.Y. (1989) and in T. J. Silhavy, M. L. Berman and L. W. Enquist, Experiments with Gene Fusions, Cold Spring Harbor Laboratory, Cold Spring Harbor, N.Y. (1984) and in Ausubel, F. M. et al., Current Protocols in Molecular Biology, Greene Publishing Assoc. and Wiley Interscience (1987).

The recombinant nucleic acid construct or gene construct is expressed in a suitable host organism by inserting it advantageously into a host-specific vector which makes optimal expression of the genes in the host possible. Vectors are well known to the skilled worker and can be found, for example, in "Cloning Vectors" (Pouwels P. H. et al., eds., Elsevier, Amsterdam-New York-Oxford, 1985).

F. Hosts which are Usable According to the Invention

It is possible with the aid of the vectors of the invention to prepare recombinant microorganisms which are transformed, for example, with at least one vector of the invention and can be used for producing the polypeptides of the invention. The above-described recombinant constructs of the invention are advantageously introduced into a suitable host system and expressed. In this context, preference is given to using cloning and transfection methods familiar to the skilled worker, such as, for example, coprecipitation, protoplast fusion, electroporation, retroviral transfection and the like, in order to express the nucleic acids mentioned in the particular expression system. Suitable systems are described, for example, in Current Protocols in Molecular Biology, F. Ausubel et al., Eds., Wiley Interscience, New York 1997, or Sambrook et al. Molecular Cloning: A Laboratory Manual. 2nd Ed., Cold Spring Harbor Laboratory, Cold Spring Harbor Laboratory Press, Cold Spring Harbor, N.Y., 1989.

According to the invention, it is also possible to prepare microorganisms by homologous recombination. For this purpose, a vector is prepared which contains at least one section of a gene of the invention or of a coding sequence, into which at least one amino acid deletion, addition or substitution has been introduced, if appropriate, in order to modify, for example to functionally disrupt, the sequence of the invention ("knockout" vector). The sequence introduced may also be, for example, a homolog from a related microorganism or may have been derived from a mammalian, yeast or insect source. Alternatively, the vector used for homologous recombination may be designed in such a way that the endogenous gene is mutated or otherwise modified upon homologous recombination, while still encoding the functional protein (for example, the upstream regulatory region may have been modified in such a way that this causes modified expression of the endogenous protein). The modified section of the gene of the invention is present in the homologous recombination vector. The construction of suitable vectors for homologous recombination is described, for example, in Thomas, K. R. and Capecchi, M. R. (1987) Cell 51:503.

Suitable recombinant host organisms for the nucleic acid of the invention or the nucleic acid construct are, in principle, all prokaryotic or eukaryotic organisms. Host organisms which are used advantageously are microorganisms such as bacteria, fungi or yeasts. Advantageously used are Gram-positive or Gram-negative bacteria, preferably bacteria of the families Enterobacteriaceae, Pseudomonadaceae, Rhizobiaceae, Streptomycetaceae and Nocardiaceae, particularly preferably bacteria of the genera *Escherichia, Pseudomonas, Streptomyces, Nocardia, Burkholderia, Salmonella, Agrobacterium* and *Rhodococcus*. Very particular preference is given to the genus and species *Escherichia coli*. In addition, further advantageous bacteria can be found in the group of alpha-proteobacteria, beta-proteobacteria or gamma-proteobacteria.

The host organism, or host organisms, according to the invention comprise at least one of the nucleic acid sequences, nucleic acid constructs or vectors which are described in the present invention and which code for an enzyme having L-carnitine dehydrogenase activity (Kleber H P (1997) FEMS Microbiology, 147, 1-9).

Depending on the host organism, the organisms used in the method of the invention are cultured or grown in a manner known to the skilled worker. Microorganisms are usually grown in a liquid medium comprising a carbon source, usually in the form of sugars, a nitrogen source, usually in the form or organic nitrogen sources such as yeast extract or of salts such as ammonium sulfate, trace elements such as salts of iron, manganese, magnesium, and, if appropriate, vitamins, at temperatures between 0° C. and 100° C., preferably between 10° C. and 60° C., while passing in oxygen. The pH of the nutrient liquid may be kept constant there, i.e. regulated or not regulated during cultivation. Cultivation may be batchwise, semibatchwise or continuous. Nutrients may be introduced at the start of the fermentation or fed in semicontinuously or continuously. The ketone may be added directly to the cultivation or, advantageously, after cultivation. The enzymes may be isolated from the organisms by the method described in the examples or used as crude extract for the reaction.

The host organisms comprise advantageously 1 U/l enzyme activity, for example L-carnitine dehydrogenase activity, preferably 100 U/l, particularly preferably more than 1000 U/l.

G. Recombinant Production of the Polypeptides

The invention furthermore relates to methods for recombinant production of polypeptides of the invention or of functional, biologically active fragments thereof, in which method a polypeptide-producing microorganism is cultured, expression of said polypeptides is induced if appropriate, and the latter are isolated from the culture. If desired, the polypeptides may also be produced on the industrial scale in this manner.

The recombinant microorganism can be cultured and fermented by known methods. For example, bacteria may be propagated in TB or LB medium and at a temperature of from 20 to 40° C. and pH 6 to 9. Suitable culturing conditions are described in detail, for example, in T. Maniatis, E. F. Fritsch and J. Sambrook, Molecular Cloning: A Laboratory Manual, Cold Spring Harbor Laboratory, Cold Spring Harbor, N.Y. (1989).

Unless the polypeptides are secreted into the culture medium, the cells are then disrupted and the product is obtained from the lysate by known protein isolation methods. The cells can be disrupted either by high-frequency ultrasound, by high pressure, for example in a French press, by osmolysis, by the action of detergents, lytic enzymes or organic solvents, by homogenizers or by combining two or more of the methods listed.

The polypeptides can be purified using known chromatographic methods such as molecular sieve chromatography (gel filtration), for example Q-Sepharose chromatography, ion exchange chromatography and hydrophobic chromatography, and also by other customary methods such as ultrafiltration, crystallization, salting out, dialysis and native gel electrophoresis. Suitable methods are described, for example, in Cooper, T. G., Biochemische Arbeitsmethoden [The Tools of Biochemistry], Verlag Walter de Gruyter, Berlin, New York or in Scopes, R., Protein Purification, Springer Verlag, New York, Heidelberg, Berlin.

It may be advantageous to isolate the recombination protein by using vector systems or oligonucleotides which extend the cDNA by particular nucleotide sequences and thus code for modified polypeptides or fusion proteins which simplify purification, for example. Suitable modifications of this kind are, for example, "tags" acting as anchors, such as, for example, the modification known as hexa-histidine anchor, or epitopes which can be recognized as antigens by antibodies (described, for example, in Harlow, E. and Lane, D., 1988, Antibodies: A Laboratory Manual. Cold Spring Harbor (N.Y.) Press). These anchors can be used for attaching the proteins to a solid support such as, for example, a polymer matrix which may be packed, for example, in a chromatography column or on a microtiter plate or on any other support.

At the same time, these anchors may also be used for identifying the proteins. Moreover, customary labels such as fluorescent dyes, enzyme labels which, after reaction with a substrate, form a detectable reaction product or radiolabels may be used, alone or in combination with said anchors, for identifying the proteins in order to derivatize said proteins.

H. Carrying Out the Method of the Invention for Preparing (S)-Alkanols

The enzymes having dehydrogenase activity may be used as free or immobilized enzyme in the method of the invention.

The method of the invention is advantageously carried out at a temperature between 0° C. and 95° C., preferably between 10° C. and 85° C., particularly preferably between 15° C. and 75° C.

The pH in the method of the invention is advantageously maintained between pH 4 and 12, preferably between pH 4.5 and 9, particularly preferably between pH 5 and 8.

In the method of the invention, enantiomerically pure or chiral products such as 3-methylamino-1-(2-thienyl)-(S)-propanol mean enantiomers which show enrichment of one enantiomer. The method preferably achieves enantiomeric purities of at least 70% ee, preferably of at least 80% ee, particularly preferably of at least 90% ee, very particularly preferably of at least 98% ee.

It is possible to use for the method of the invention growing cells which comprise the nucleic acids, nucleic acid constructs or vectors of the invention. It is also possible to use resting or disrupted cells. Disrupted cells mean, for example, cells which have been made permeable by treatment with, for example, solvents, or cells which have been ruptured by an enzyme treatment, by a mechanical treatment (for example French Press or ultrasound) or by another method. The crude extracts obtained in this way are advantageously suitable for the method of the invention. Purified or partially purified enzymes may also be used for the method. Likewise suitable are immobilized microorganisms or enzymes which can advantageously be utilized in the reaction.

If free organisms or enzymes are used for the method of the invention, these are expediently removed, for example by filtration or centrifugation, before the extraction.

The product prepared in the method of the invention, such as 3-methylamino-1-(2-thienyl)-(S)-propanol, can advantageously be isolated from the aqueous reaction solution by extraction or distillation or, advantageously, by extraction and distillation. The extraction can be repeated several times to increase the yield. Examples of suitable extractants are solvents such as toluene, methylene chloride, butyl acetate, diisopropyl ether, benzene, MTBE or ethyl acetate, without being limited thereto.

After concentration of the organic phase, the products can usually be obtained in good chemical purities, i.e. greater than 80% chemical purity. After extraction, the organic phase containing the product can, however, also be only partly concentrated, and the product can be crystallized out. For this purpose, the solution is advantageously cooled to a temperature of from 0° C. to 10° C. Crystallization is also possible directly from the organic solution or from an aqueous solution. The crystallized product can be taken up again in the same or in a different solvent for recrystallization and be crystallized again. It is possible, by carrying out the subsequent advantageous crystallization at least once, to increase the enantiomeric purity of the product further if necessary.

With the types of workup mentioned, the product of the method of the invention can be isolated in yields of from 60 to 100%, preferably from 80 to 100%, particularly preferably from 90 to 100%, based on the substrate employed for the reaction, such as 3-methylamino-1-(2-thienyl)-propan-1-one, for example. The isolated product is distinguished by a high chemical purity of >90%, preferably >95%, particularly preferably >98%. Furthermore, the products have a high enantiomeric purity which can advantageously be further increased, if necessary, by said crystallization.

The method of the invention can be carried out batchwise, semibatchwise or continuously.

The method may advantageously be carried out in bioreactors as described, for example, in Biotechnology, Volume 3, 2nd Edition, Rehm et al. Eds., (1993), in particular Chapter II.

The description above and the examples below serve only to illustrate the invention. The invention likewise comprises the numerous possible modifications obvious to the skilled worker.

EXPERIMENTAL SECTION

Example 1

Relative activity of the dehydrogenases of the invention for various substrates (optical purity in % ee is indicated in brackets)

| Substrate | ADH-3 enzyme SEQ ID NO: 2 | ADH-4 enzyme SEQ ID NO: 4 | Comparative enzyme EP 1152054 SEQ ID NO: 1 |
|---|---|---|---|
| Acetophenone | 16.08 (>99%) | 3.14 (70%) | 0.84 (>99%) |
| m-DICAP | 100 (>99%) | 56.38 (12%) | 2.3 (>99%) |
| CMAP | 34.46 (90%) | 24.89 (88%) | 29.44 (98%) |

The reaction was carried out without cofactor regeneration.
Reaction Mixture:
180 µl of 50 mM Kpi buffer, including 1 mM MgCl2
20 µl of enzyme solution
200 µl of NADPH, 10 mM stock solution
100 µl of substrate, 1 M stock solution 500 µl of hexane The reaction mixture was incubated at 37° C. and 1000 rpm for approx. 20 hours. It was then centrifuged at 20° C., the clear supernatant was removed and analyzed by chiral gas chromatography.

Example 2

Relative activity of the dehydrogenases of the invention for various substrates (optical purity in % ee is indicated in brackets) with cofactor regeneration.

The reaction was carried out in a manner similar to example 1. Cofactor regeneration was carried out by way of addition of glucose and glucose dehydrogenase in a monophasic liquid system.

| Substrate | ADH-3 enzyme SEQ ID NO: 2 | ADH-4 enzyme SEQ ID NO: 4 | Comparative enzyme EP 1152054 SEQ ID NO: 1 |
|---|---|---|---|
| Acetophenone | 8.9 (>99% S) | not determined | 0.7 (>99% S) |
| m-DICAP | 100 (>99% R) | 55.8 (25% S) | 47.1 (93% R) |
| p-DICAP | 18.9 (>99% R) | 62.1 (44% S) | 62.5 (>99% R) |
| FCA | 99.5 (>99% R) | 53.6 (58% S) | 50.4 (>99% R) |

Example 3

Relative activity of the dehydrogenases of the invention for various substrates (optical purity in % ee is indicated in brackets) with cofactor regeneration in the 2-phase system.

The reaction was carried out in a manner similar to example 2. Cofactor regeneration was carried out by way of addition of glucose and glucose dehydrogenase in a two-phase liquid system (MTBE: aqueous).

| Substrate | ADH-3 enzyme SEQ ID NO: 2 | ADH-4 enzyme SEQ ID NO: 4 | Comparative enzyme EP 1152054 SEQ ID NO: 1 |
|---|---|---|---|
| Acetophenone | 71.2 (>99% S) | 0.4 (70% S) | 0.2 (>99% S) |
| m-DICAP | 100 (>99% R) | 24.6 (6% S) | 14 (>99% R) |
| p-DICAP | 30.4 (>99% R) | 27.6 (42% S) | 24.2 (>99% R) |
| FCA | 99.5 (>99% R) | 15.3 (46% S) | 12.6 (>99% R) |
| CMAP | 100 (>99% R) | 77.1 (97% S) | 46.8 (>99% R) |

Abbreviations:
m-DICAP: 2,3'-dichloro-acetophenone
p-DICAP: 2,4'-dichloro-acetophenone
FCA: 4'-fluoro-2-chloro-acetophenone
CMAP: 4-chloro-methoxyacetophenone

We claim:

1. A method for the microbiological preparation of a substituted alkanol of formula I

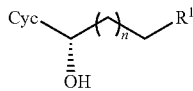
(I)

in which
n is an integer from 0 to 5;
Cyc is an optionally-substituted mononuclear or polynuclear, saturated or unsaturated, carbocyclic or heterocyclic ring, and
$R^1$ is a halogen, SH, OH, $NO_2$, $NR^2R^3$ or $NR^2R^3R^{4+}X^-$, whereby $R^2$, $R^3$ and $R^4$ independently are H or a lower alkyl or a lower alkoxy radical and $X^-$ is a counterion,
wherein, in a medium comprising an alkanone of formula II

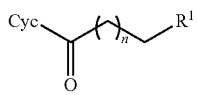
(II)

in which n, Cyc and $R^1$ are as defined above, the method comprises
a) culturing a microorganism, whereby the microorganism produces a dehydrogenase having the amino acid sequence of SEQ ID NO: 2, and wherein the dehydrogenase reduces 3-methylamino-1-(2-thienyl)-propan-1-one to the corresponding S-alcohol with at least 50% of the activity of the dehydrogenase having the amino acid sequence of SEQ ID NO: 2, or
b) incubating the dehydrogenase of a), whereby the dehydrogenase catalyzes enzymatic reduction of the compound of formula II to the compound of formula I; and
c) isolating the reduced compound of formula I.

2. The method of claim 1, wherein the dehydrogenase catalyzes enantioselective synthesis of the compound of formula I.

3. The method of claim 1, wherein the compound of formula I is 3-methylamino-1-(2-thienyl)-(S)-propanol of formula III

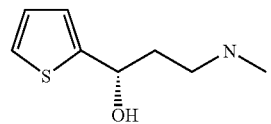
(III)

and the compound of the formula II is 3-methylamino-1-(2-thienyl)-propan-2-one of formula IV

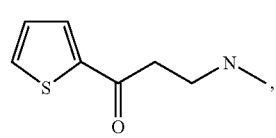
(IV)

and the isolated reduced compound of formula I is essentially enantiomerically pure.

4. The method of claim 1, wherein the dehydrogenase is encoded by a nucleic acid comprising a nucleic acid sequence that is at least 80% identical to the nucleic acid sequence of SEQ ID NO: 1.

5. The method of claim 1, wherein the culturing or incubating is carried out with an addition of reduction equivalents or is carried out under conditions in which reduction equivalents consumed are regenerated.

6. The method of claim 1, wherein the microorganism is selected from the group consisting of the families Enterobacteriaceae, Pseudomonadaceae, Rhizobiaceae, Streptomycetaceae and Nocardiaceae.

7. The method of claim 1, wherein the microorganism is a recombinant microorganism that has been transformed with a nucleic acid construct coding for the dehydrogenase.

8. The method of claim 1, wherein the method comprises preparing Duloxetine.

9. The method of claim 3, wherein the method comprises preparing Duloxetine.

10. The method of claim 4, wherein the nucleic acid comprises the nucleic acid sequence of SEQ ID NO: 1.

* * * * *

SEQUENCE LISTING

<160> NUMBER OF SEQ ID NOS: 5

<210> SEQ ID NO 1
<211> LENGTH: 723
<212> TYPE: DNA
<213> ORGANISM: Candida magnoliae
<220> FEATURE:
<221> NAME/KEY: CDS
<222> LOCATION: (1)..(723)
<223> OTHER INFORMATION: ADH-R

<400> SEQUENCE: 1

```
atg acg act act tca aat gcg ctc gtc act gga ggc agc cgc ggc att    48
Met Thr Thr Thr Ser Asn Ala Leu Val Thr Gly Gly Ser Arg Gly Ile
1               5                   10                  15 ggc gct gct tcc gcc att aag ctg gct cag gag ggc tac agt gtt acg    96
Gly Ala Ala Ser Ala Ile Lys Leu Ala Gln Glu Gly Tyr Ser Val Thr
            20                  25                  30 ctg gcc tct cgc agt gtt gat aaa ctg aat gaa gta aag gcg aaa ctc   144
Leu Ala Ser Arg Ser Val Asp Lys Leu Asn Glu Val Lys Ala Lys Leu
        35                  40                  45 cca att gta cag gac ggg cag aag cac tac att tgg gaa ctc gat ctg   192
Pro Ile Val Gln Asp Gly Gln Lys His Tyr Ile Trp Glu Leu Asp Leu
50                  55                  60 gct gat gtg gaa gct gct tcg tcg ttc aag ggt gct cct ttg cct gct   240
Ala Asp Val Glu Ala Ala Ser Ser Phe Lys Gly Ala Pro Leu Pro Ala
65                  70                  75                  80 agc agc tac gac gtc ttc gtt tcg aac gcg ggc gtc gct gcg ttc tcg   288
Ser Ser Tyr Asp Val Phe Val Ser Asn Ala Gly Val Ala Ala Phe Ser
                85                  90                  95 ccc aca gcc gac cac gat gat aag gag tgg cag aac ttg ctc gcc gtg   336
Pro Thr Ala Asp His Asp Asp Lys Glu Trp Gln Asn Leu Leu Ala Val
            100                 105                 110 aac ttg tcg tcg ccc att gcc ctc acg aag gcc ctc ttg aag gac gtc   384
Asn Leu Ser Ser Pro Ile Ala Leu Thr Lys Ala Leu Leu Lys Asp Val
        115                 120                 125 tcc gaa agg cct gcg gac aat ccg ttg cag att atc tac att tcg tcg   432
Ser Glu Arg Pro Ala Asp Asn Pro Leu Gln Ile Ile Tyr Ile Ser Ser
130                 135                 140 gtg gcc ggc ttg cat ggc gcc gcg cag gtc gcc gtg tac agt gca tct   480
Val Ala Gly Leu His Gly Ala Ala Gln Val Ala Val Tyr Ser Ala Ser
145                 150                 155                 160 aag gcc ggt ctt gat ggt ttt atg cgc tcc gtc gcc cgt gag gtg ggc   528
Lys Ala Gly Leu Asp Gly Phe Met Arg Ser Val Ala Arg Glu Val Gly
                165                 170                 175 ccg aag ggc atc cat gtg aac tcc atc aac ccc gga tac acc aag act   576
Pro Lys Gly Ile His Val Asn Ser Ile Asn Pro Gly Tyr Thr Lys Thr
            180                 185                 190 gaa atg acc gcg ggc att gaa gcc ctg cct gat ttg cct atc aag ggg   624
Glu Met Thr Ala Gly Ile Glu Ala Leu Pro Asp Leu Pro Ile Lys Gly
        195                 200                 205 tgg atc gag ccc gag gca att gct gac gcg gtt ctg ttt ctg gca aag   672
Trp Ile Glu Pro Glu Ala Ile Ala Asp Ala Val Leu Phe Leu Ala Lys
    210                 215                 220 tcc aag aat atc acc ggc aca aac att gtg gtc gac aat ggc ttg att   720
Ser Lys Asn Ile Thr Gly Thr Asn Ile Val Val Asp Asn Gly Leu Ile
225                 230                 235                 240 gct                                                                723
Ala

<210> SEQ ID NO 2
<211> LENGTH: 241
<212> TYPE: PRT
<213> ORGANISM: Candida magnoliae

<400> SEQUENCE: 2

Met Thr Thr Thr Ser Asn Ala Leu Val Thr Gly Gly Ser Arg Gly Ile
1               5                   10                  15

Gly Ala Ala Ser Ala Ile Lys Leu Ala Gln Glu Gly Tyr Ser Val Thr
            20                  25                  30

Leu Ala Ser Arg Ser Val Asp Lys Leu Asn Glu Val Lys Ala Lys Leu
        35                  40                  45
```

```
Pro Ile Val Gln Asp Gly Gln Lys His Tyr Ile Trp Glu Leu Asp Leu
    50                  55                  60

Ala Asp Val Glu Ala Ala Ser Ser Phe Lys Gly Ala Pro Leu Pro Ala
65                  70                  75                  80

Ser Ser Tyr Asp Val Phe Val Ser Asn Ala Gly Val Ala Ala Phe Ser
                85                  90                  95

Pro Thr Ala Asp His Asp Asp Lys Glu Trp Gln Asn Leu Leu Ala Val
            100                 105                 110

Asn Leu Ser Ser Pro Ile Ala Leu Thr Lys Ala Leu Leu Lys Asp Val
        115                 120                 125

Ser Glu Arg Pro Ala Asp Asn Pro Leu Gln Ile Ile Tyr Ile Ser Ser
    130                 135                 140

Val Ala Gly Leu His Gly Ala Ala Gln Val Ala Val Tyr Ser Ala Ser
145                 150                 155                 160

Lys Ala Gly Leu Asp Gly Phe Met Arg Ser Val Ala Arg Glu Val Gly
                165                 170                 175

Pro Lys Gly Ile His Val Asn Ser Ile Asn Pro Gly Tyr Thr Lys Thr
            180                 185                 190

Glu Met Thr Ala Gly Ile Glu Ala Leu Pro Asp Leu Pro Ile Lys Gly
        195                 200                 205

Trp Ile Glu Pro Glu Ala Ile Ala Asp Ala Val Leu Phe Leu Ala Lys
    210                 215                 220

Ser Lys Asn Ile Thr Gly Thr Asn Ile Val Val Asp Asn Gly Leu Ile
225                 230                 235                 240

Ala

<210> SEQ ID NO 3
<211> LENGTH: 723
<212> TYPE: DNA
<213> ORGANISM: Candida magnoliae
<220> FEATURE:
<221> NAME/KEY: CDS
<222> LOCATION: (1)..(723)
<223> OTHER INFORMATION: ADH-L

<400> SEQUENCE: 3 atg aca tct aca cct aat gcc ctt gtc acg gga ggc agc cgc ggc att     48
Met Thr Ser Thr Pro Asn Ala Leu Val Thr Gly Gly Ser Arg Gly Ile
1               5                   10                  15 ggc gct tcc gcc gcc atc aag ctg gct caa gaa ggg tac agc gtc acg     96
Gly Ala Ser Ala Ala Ile Lys Leu Ala Gln Glu Gly Tyr Ser Val Thr
                20                  25                  30 ctg gcg tcc cgc gac ctt gag aaa ctt aac gag gtc aag gac aag ctg    144
Leu Ala Ser Arg Asp Leu Glu Lys Leu Asn Glu Val Lys Asp Lys Leu
            35                  40                  45 cca atc gtg agg ggt gga cag aaa cac tac gtt tgg caa ctc gat ctt    192
Pro Ile Val Arg Gly Gly Gln Lys His Tyr Val Trp Gln Leu Asp Leu
    50                  55                  60 gcc gat gta ttg gct gca tcg tct ttc aag gcg gct cct ctg ccg gcc    240
Ala Asp Val Leu Ala Ala Ser Ser Phe Lys Ala Ala Pro Leu Pro Ala
65                  70                  75                  80 agc agc tac gat ttg ttt gtt tcg aac gcc gga att gcc cag ttc tcg    288
Ser Ser Tyr Asp Leu Phe Val Ser Asn Ala Gly Ile Ala Gln Phe Ser
                85                  90                  95 ccc acg gca gag tat act aat agt gag tgg ctg aac att atg acc att    336
Pro Thr Ala Glu Tyr Thr Asn Ser Glu Trp Leu Asn Ile Met Thr Ile
            100                 105                 110
```

-continued

| | | |
|---|---|---|
| aac tta gtg tcc ccg att gcc ctg acg aag gct ctt ttg cag gcc gtt<br>Asn Leu Val Ser Pro Ile Ala Leu Thr Lys Ala Leu Leu Gln Ala Val<br>115     120     125 | | 384 |
| tct ggg agg tcg agc gag aac ccg ttt cag atc gta ttc atc tcg tcg<br>Ser Gly Arg Ser Ser Glu Asn Pro Phe Gln Ile Val Phe Ile Ser Ser<br>130     135     140 | | 432 |
| gtt gca gca cta cgt ggc gtt gca caa acg gcc gtc tac agt gcg tcg<br>Val Ala Ala Leu Arg Gly Val Ala Gln Thr Ala Val Tyr Ser Ala Ser<br>145      150     155     160 | | 480 |
| aag gct ggt act gat gga ttc gca cgc tca ctt gct cgc gaa cta ggt<br>Lys Ala Gly Thr Asp Gly Phe Ala Arg Ser Leu Ala Arg Glu Leu Gly<br>     165     170     175 | | 528 |
| cct caa ggc gtc cat gtg aac gtg gtg aac cct ggc tgg act aag aca<br>Pro Gln Gly Val His Val Asn Val Val Asn Pro Gly Trp Thr Lys Thr<br>      180     185     190 | | 576 |
| gac atg acg gaa gga gtc gaa acc cca aag gac atg ccc att aag ggc<br>Asp Met Thr Glu Gly Val Glu Thr Pro Lys Asp Met Pro Ile Lys Gly<br>     195     200     205 | | 624 |
| tgg atc cag cct gag gca att gct gat gct gta gta ttc ctt gcg agg<br>Trp Ile Gln Pro Glu Ala Ile Ala Asp Ala Val Val Phe Leu Ala Arg<br>210     215     220 | | 672 |
| tcg aaa aac att acc ggc gcg aat att gta gtg gac aat ggt ttc tcg<br>Ser Lys Asn Ile Thr Gly Ala Asn Ile Val Val Asp Asn Gly Phe Ser<br>225     230     235     240 | | 720 |
| acg<br>Thr | | 723 |

<210> SEQ ID NO 4
<211> LENGTH: 241
<212> TYPE: PRT
<213> ORGANISM: Candida magnoliae

<400> SEQUENCE: 4

Met Thr Ser Thr Pro Asn Ala Leu Val Thr Gly Gly Ser Arg Gly Ile
1       5       10       15

Gly Ala Ser Ala Ala Ile Lys Leu Ala Gln Glu Gly Tyr Ser Val Thr
       20       25       30

Leu Ala Ser Arg Asp Leu Glu Lys Leu Asn Glu Val Lys Asp Lys Leu
     35       40       45

Pro Ile Val Arg Gly Gly Gln Lys His Tyr Val Trp Gln Leu Asp Leu
  50       55       60

Ala Asp Val Leu Ala Ala Ser Ser Phe Lys Ala Ala Pro Leu Pro Ala
65       70       75       80

Ser Ser Tyr Asp Leu Phe Val Ser Asn Ala Gly Ile Ala Gln Phe Ser
       85       90       95

Pro Thr Ala Glu Tyr Thr Asn Ser Glu Trp Leu Asn Ile Met Thr Ile
       100      105      110

Asn Leu Val Ser Pro Ile Ala Leu Thr Lys Ala Leu Leu Gln Ala Val
     115      120      125

Ser Gly Arg Ser Ser Glu Asn Pro Phe Gln Ile Val Phe Ile Ser Ser
  130      135      140

Val Ala Ala Leu Arg Gly Val Ala Gln Thr Ala Val Tyr Ser Ala Ser
145      150      155      160

Lys Ala Gly Thr Asp Gly Phe Ala Arg Ser Leu Ala Arg Glu Leu Gly
       165      170      175

Pro Gln Gly Val His Val Asn Val Val Asn Pro Gly Trp Thr Lys Thr
     180      185      190

```
Asp Met Thr Glu Gly Val Glu Thr Pro Lys Asp Met Pro Ile Lys Gly
            195                 200                 205

Trp Ile Gln Pro Glu Ala Ile Ala Asp Ala Val Val Phe Leu Ala Arg
            210                 215                 220

Ser Lys Asn Ile Thr Gly Ala Asn Ile Val Val Asp Asn Gly Phe Ser
225                 230                 235                 240

Thr

<210> SEQ ID NO 5
<211> LENGTH: 241
<212> TYPE: PRT
<213> ORGANISM: Candida magnoliae

<400> SEQUENCE: 5

Met Ser Thr Pro Leu Asn Ala Leu Val Thr Gly Ala Ser Arg Gly Ile
1               5                   10                  15

Gly Ala Ala Thr Ala Ile Lys Leu Ala Glu Asn Gly Tyr Ser Val Thr
            20                  25                  30

Leu Ala Ala Arg Asn Val Ala Lys Leu Asn Glu Val Lys Glu Lys Leu
        35                  40                  45

Pro Val Val Lys Asp Gly Gln Lys His His Ile Trp Glu Leu Asp Leu
    50                  55                  60

Ala Ser Val Glu Ala Ala Ser Ser Phe Lys Gly Ala Pro Leu Pro Ala
65                  70                  75                  80

Ser Asp Tyr Asp Leu Phe Val Ser Asn Ala Gly Ile Ala Gln Phe Thr
                85                  90                  95

Pro Thr Ala Asp Gln Thr Asp Lys Asp Phe Leu Asn Ile Leu Thr Val
            100                 105                 110

Asn Leu Ser Ser Pro Ile Ala Leu Thr Lys Ala Leu Leu Lys Gly Val
        115                 120                 125

Ser Glu Arg Ser Asn Glu Lys Pro Phe His Ile Ile Phe Leu Ser Ser
    130                 135                 140

Ala Ala Ala Leu His Gly Val Pro Gln Thr Ala Val Tyr Ser Ala Ser
145                 150                 155                 160

Lys Ala Gly Leu Asp Gly Phe Val Arg Ser Leu Ala Arg Glu Val Gly
                165                 170                 175

Pro Lys Gly Ile His Val Asn Val Ile His Pro Gly Trp Thr Lys Thr
            180                 185                 190

Asp Met Thr Asp Gly Ile Asp Asp Pro Asn Thr Pro Ile Lys Gly
            195                 200                 205

Trp Ile Gln Pro Glu Ala Ile Ala Asp Ala Val Val Phe Leu Ala Lys
            210                 215                 220

Ser Lys Asn Ile Thr Gly Thr Asn Ile Val Val Asp Asn Gly Leu Leu
225                 230                 235                 240

Ala
```